(12) United States Patent
Kirschbaum et al.

(10) Patent No.: US 6,174,722 B1
(45) Date of Patent: Jan. 16, 2001

(54) IN-VITRO TRANSCRIPTION PROCESSES FOR SCREENING NATURAL PRODUCTS AND OTHER CHEMICAL SUBSTANCES

(75) Inventors: Bernd Kirschbaum, Mainz; Wilhelm Stahl, Idstein; Irvin Winkler, Liederbach; Michael Meisterernst, Eichenau, all of (DE)

(73) Assignee: Aventis Pharma Deutschland GmbH (DE)

( * ) Notice: Under 35 U.S.C. 154(b), the term of this patent shall be extended for 0 days.

(21) Appl. No.: 09/038,141

(22) Filed: Mar. 11, 1998

(30) Foreign Application Priority Data

Mar. 12, 1997 (DE) .............................................. 197 10 159

(51) Int. Cl.$^7$ ........................... C12N 15/63; C12N 15/64; C12Q 1/68; G01N 33/53; C07H 21/04

(52) U.S. Cl. ............................ 435/320.1; 435/6; 435/7.1; 435/91.4; 536/23.1

(58) Field of Search ................................ 435/6, 7.1, 91.4; 536/320.1, 23.1

(56) References Cited

U.S. PATENT DOCUMENTS 5,563,036   10/1996   Peterson et al. ......................... 435/6

FOREIGN PATENT DOCUMENTS

WO 96/26959   9/1996   (WO) .

OTHER PUBLICATIONS

Bellorini et al NAR vol. 23 No. 10 pp. 1657–1663, 1995.*
Ausubel et al Curr. Prot. in M.B. Chapter 4, 1989.*
Du et al EMBO vol. 12 No. 2 pp. 501–511, 1993.*
Mischiati et al Biotechniques vol. 15 nO. 1, 1993.*
Sambrook et al Mol. Cloning a Lab Manual section 7.6–7.7 & B.16, 1989.*
Annweiler et al JBC vol. 268 No. 4 pp. 2525–2534, 1993.*
Reifenrath–Biesel et al Gene 181 pp. 135–137, 1996.*
Smith et al NAR vol. 15 (12) pp4991, 1987.*
Kaiser EMBO vol. 14 (14) pp 3520–3527, 1995.*
L. Zawel et al., "Common Themes in Assembly and Function of Eukaryotic Transcription Complexes", Annu. Reg. Biochem., 1995, 64:533–61.
P. Weil et al., "Selective and Accurate Initiation of Transcription at the Ad2 Major Late Promoter in a Soluble System Dependent on Purified RNA Polymerase II and DNA", Cell, vol. 14, 1979, p. 469–84.
P. Weil et al., "Faithful Transcription of Eukaryotic Genes by RNA Polymerase III in Systems Reconstituted with Purified DNA Templates", The Journal of Biological Chemistry, vol. 254, No. 13, 1979, pp. 6163–6173.
C. Verrijzer et al., "TAFs Mediate Transcriptional Activation and Promoter Selectivity", Reviews, Sep. 1996, pp. 338–341.
A. Goppelt et al., "A Mechanism for Repression of Class II Gene Transcription Through Specific Binding of NC2 to TBP–promoter Complexes via Heterodimeric Histone Fold Domains", The EMBO Journal, vol. 15, No. 12, 1996, pp. 3105–3116.

(List continued on next page.)

Primary Examiner—Kenneth R. Horlick
Assistant Examiner—Jeffrey Siew
(74) Attorney, Agent, or Firm—Foley & Lardner

(57) ABSTRACT

An process for analyzing transcription which can be automated and which is suitable for bulk screening. The process involves transcribing a DNA sequence using a nuclear extract, which can be complemented or fully replaced by exogenous transcription factors and/or cofactors; optionally removing the proteins of the reaction mixture; binding the resulting transcript to a solid matrix; removing the excess labeled nucleotides; and determining the amount of labeled transcript. Methods of using the inventive process to identify compounds having a selective effect on gene expression.

8 Claims, 3 Drawing Sheets

OTHER PUBLICATIONS

M. Kretzchmar et al., "A Novel Mediator of Class II Gene Transcription with Homology to Viral Immediate–Early Transcriptional Regulators", Cell, vol. 78, 1994, pp. 525–534.

Jun Liu, "FK506 and Cyclosporin, Molecular Probes for Studying Intracellular Signal Transduction", Immunology Today, vol. 14, No. 6, 1993, pp. 290–295.

M. Meisterernst et al., "Activation of Class II Gene Transcription by regulatory Factors is Potentiated by a Novel Activity", Cell, vol. 66, 1991, pp. 981–993.

K. Kaiser et al., "The Human General Co–factors", Reviews, Sep. 1996, pp. 342–345.

K. Kaiser et al., "The Coactivator p15 (PC4) Initiates Transcriptional Activation during TFIIA–TFIID–promoter Complex Formation", The EMBO Journal, vol. 14, No. 14, 1995, pp. 3520–3527.

Y. Ohkuma et al., "Factors Involved in specific Transcription by Mamalian RNA Polymerase II: Purification and Characterization of General Transcription Factor TFIIE", Proc. Natl. Acad. Sci., vol. 87, 1990, pp. 9163–9167.

R. Roeder, "Multiple Forms of Deoxyribonucleic Acid–dependent Ribonucleic Acid Polymerase in *Xenopus laevis*", The Journal of Biological Chemistry, vol. 249, No. 1, 1974, pp. 241–248.

M. Sawadogo et al., "Factors Involved in Specific Transcription by Human RNA Polymerase II: Analysis by a Rapid and Quantitative in vitro Assay", Proc. Natl. Acad. Sci. USA, vol. 82, Jul. 1985, pp. 4394–4398.

R. Scheinman et al., "Role of Transcriptional Activation of $I_kB\alpha$ in Mediation of Immunosuppression by Glucocorticoids", Science, vol. 270, Oct. 1995, pp. 283–286.

J. Dignam et al., "Accurate Transcription Initiation by RNA Polymerase II in a Soluble Extract from Isolated Mammalian Nuclei", Nucleic Acids Research, vol. 11, No. 5, 1983, pp. 1475–1489.

N. Auphan et al., "Immunosuppression by Glucocorticoids: Inhibition of $NF_{-k}B$ Activity Through Induction of $I_kB$ Synthesis", Science, vol. 270, Oct. 1995, pp. 286–290.

J. Dignam et al., "Eukaryotic Gene Transcription with Purified Components", Methos in Ensymology, vol. 101, 1983, pp. 582–599.

* cited by examiner

IN-VITRO TRANSCRIPTION PROCESSES FOR SCREENING NATURAL PRODUCTS AND OTHER CHEMICAL SUBSTANCES

FIELD OF THE INVENTION

The invention relates to an in-vitro process for analyzing transcription of viral and cellular genes which can be automated and which is suitable for efficient and economical bulk screening with the aim of finding specific chemical lead structures which have a selective effect on gene activity.

BACKGROUND OF THE INVENTION

Screening natural products for bioactive constituents experienced an upswing after it had emerged that rational design of active substances alone does not allow a successful search for active substances. Thus, research focuses not only on libraries of chemical substances and combinatory libraries, but, yet again, on traditional extracts of natural products as sources for substances. This is due mainly to the diversity of the substances which these extracts contain. Model analytical methods prove that extracts of microbial fermentations contain approximately 500 classes of compounds, which differ greatly in their structure. As regards their diversity, they are thus far superior to chemical and combinatory substance libraries.

A factor which limits the pharmacological exploitation of the varied, and as yet largely unresearched, potential of natural products is the number of compatible, meaningful processes with which candidate active substances can be tested. In particular, processes are required which can be employed for identifying highly-specific pharmacologically active substances whose application entails a minimum of side effects.

The process described hereinbelow is based on an approach where substances are tested for their potential of engaging in the very first step of converting genetic information, i.e. the regulation of gene transcription. Such a process is intended to identify substances with direct or indirect, positive or negative effects on transcription.

The transcription strength of a gene is determined by the gene-regulatory elements of this gene, in particular by the promoter, by enhancers or by silencers. The action of the gene-regulatory elements is mediated and converted by transcription factors and cofactors. These transcription factors can have a negative or else positive effect on the transcription rate of a gene and thus contribute to the transcription strength. In the meantime, a large number of transcription factors have been identified as important "molecular switches" in the course of a large number of cellular processes, including signal transduction, cell-cycle control, differentiation and controlled cell death (apoptosis).

Most of the signals, received by the cell, which affect the transcription strength of genes are "registered" by transmembrane proteins, transmitted intracellularly by means of signal transduction chains and converted by transcription factors. Examples of proteins which receive external signals are cAMP-binding proteins, sensors for growth signals (such as the serum response factor, SRF), hormone receptors or transcription factors which participate in cytokin expression, so-called STAT proteins (signal transducers and activators of transcription).

In the meantime, a multiplicity of substances are known which have a direct or indirect effect on the transcription strength of genes. Such substances are employed, inter alia, as pharmacologically active substances in pharmaceuticals, even though the action of these substances is frequently not specific. Taking such pharmaceuticals therefore frequently entails undesired side-effects.

For example, immunological diseases are treated with pharmaceuticals which comprise cyclosporin and steroid derivatives as active substances. Cyclosporin A forms a complex with cyclophilin. The latter inhibits calcineurin, a ubiquitous phosphatase, which dephosphorylates proteins via various metabolic routes. Calcineurin regulates, for example, the transport of a subunit of the transcription factor NFAT from the cytosol into the nucleus (Liu, J. (1993) Immunology Today 14, 290–295). NFAT (nuclear factor of activated T-cells) participates in activation of some immunologically relevant genes. Cyclosporin A (CsA) indirectly regulates expression of these genes via its effect on NFAT (nuclear factor of activated T-cells). However, since cyclosporin A only indirectly regulates NFAT activity, viz. via the ubiquitous calcineurin, cyclosporin A also acts as a vasoconstrictor and as a nephro- and neurotoxin, via other metabolic routes. If a pharmacologically active substance were known with which NFAT could be inhibited specifically, possibly directly, then a medicine containing this active substance would probably cause fewer side-effects.

The pharmacologically active substances which, besides the desired effect, also entail potent side-effects, also include glucocorticoids. Glucocorticoids have been employed for many years in the standard therapy of allergies, rheumatism, inflammations and other diseases caused by an overreactive immune system. They cause, inter alia, inhibition of the activation of the cell-type-specific transcription factor NfkB (Scheinmann, R. I., Cogswell, P. C., Lofquist, A. K. & Baldwin Jr., A. S. (1995) Science 270, 283–286; Auphan, N., DiDonato, J. A., Rosette, C., Helmberg, A. & Karin M. (1995) Science 270, 286–290) by stimulating the formation of a cellular NFκB inhibitor, viz. IκB protein. IκB, in turn, prevents the transfer of active NFκB dimers into the nucleus and thus the activation of important immunological target genes. Similarly to what has been said for CsA, the effect of glucocorticoids on gene expression is relatively unspecific since glucocorticoids act not only on NFκB, but also on other proteins.

These examples make it clear that there exists a great demand for pharmacologically active substances whose profile of action is as specific as possible. To find novel chemical lead structures which have such properties, a great number of substances must be tested for their specific activity.

Despite an identical genetic make-up, individual cells always express specific proteins only, depending on the cell type and/or certain diseases or defects and the respective degree to which these cells are developed and differentiated. The basis of this individuality of cells is considered to be the specific repertoire of gene-regulatory proteins, for example the cell-type-specific and development-specific make-up which provides certain transcription factors and cofactors (accessory proteins) which regulate the coordinated and controlled transcription of distinct genes.

Specific pharmacologically active substances should therefore provide the selective activation or inhibition of the transcription of pathologically relevant genes in cells of a defined type. To identify such active substances, a transcription process is required in which the effect of candidate active substances on the transcription of individual genes, i.e. on the proteins which participate in transcriptional regulation and on the gene-regulatory elements, can be measured directly under defined conditions. Since a multiplicity of candidate active substances must be tested, other prerequisites would be that the process is simple to carry out and that it can be automated.

The first cell-free transcription process was described by Weil et al. (Weil, P. A., Luse, D. S., Segall, J., Roeder, R. G. (1979) Cell 18, 469–484). In this process, concentrated extracts from cell nuclei (so-called S100 extracts) (Weil, P. A., Segall, J., Harris, B. Ng, S. Y., Roeder, R. G. (1979) J. Biol. Chem. 254, 6163–6173), and purified RNA polymerase II were employed for the in-vitro transcription. Without exogenous RNA polymerase II, these concentrated, but not further purified, nuclear extracts were not capable of transcription (Weil, P. A., Luse, D. S., Segall, J., Roeder, R. G. (1979) Cell 18, 469–484; Dignam, J. D., Martin, P. L., Shastry, B. S., Roeder, R. G. (1983) Methods in Enzymology 101, 582–598).

Starting from such nuclear extracts, processes were subsequently developed by means of which transcription factors were isolated using several purification steps. These processes include, inter alia, purification steps in which the nuclear extracts are purified by chromatography over materials which bind nuclear proteins, such as, for example, phosphocellulose columns. Within the scope of these complicated processes which involve several steps, Dignam et al. were the first to describe the use of the commercially available P11® Systems (Whatman, Maidstone, England) for one of the purification steps (Dignam. J. D., Martin, P. L., Shastry, B. S., Roeder, R. G. (1983) Methods in Enzymology 101, 582–598).

These purification processes which include several steps were better and better adapted so that it is now possible to isolate, via complicated processes, individual transcription factors from the extracts of cell nuclei. In addition, individual factors, or their subunits, are now also available in recombinant form, such as, for example, TFIIA, TFIIB, TFIIEα, TFIIEβ and TFIIF (Zawel, L. and Reinberg, D. (1995) Annu Rev. Biochem. 64, 533–561).

At present, there therefore already exist transcription systems which are composed of a mixture of recombinant and natural purified factors. However, such transcription systems are too complicated from the technological point of view and too expensive for a screening process with high sample throughput. In contrast, in other transcription systems, for example those which use extracts from cell nuclei instead of recombinant or purified factors, a large number of secondary reactions can be found. In insufficiently or not purified nuclear extracts (crude extracts), it is mainly the nucleic acids and DNA-binding proteins, for example repressors such as histones, which have an adverse effect on the in-vitro transcription. Amongst the nucleic acids found in the crude extracts, it is in particular the DNA sequences encoding t-RNAs which have adverse effects. Since the genes for t-RNAs are transcribed approximately 100 times stronger than those of mRNAs, these t-RNA-encoding sequences lead to an excess of unspecific transcripts. The unspecific transcripts then have to be eliminated by complicated purification steps before the specific transcripts can be detected.

To allow quantitative analysis of the results of in-vitro transcriptions, vectors were developed whose DNA sequence to be transcribed lacks guanine bases (a so-called G-free sequence or G-free cassette), it being possible, if appropriate, for the G-free sequence to be followed by a segment of sequences which contains a large number of guanines. The use of these vectors allows the transcription to be carried out in the absence of GTP. Thus, only G-free sequences, but not other sequences which contain G, are transcribed. This gives specific transcripts which, in addition, are (virtually) uniform in length. Sawadogo and Roeder were the first to describe the use of a vector for transcriptions where a 400-nucleotide-long sequence is under the control of the ML (adenovirus major late) promoter. This vector gives transcripts of a length of approximately 400 nucleotides (Sawadogo, M. and Roeder, R. G. (1985) Proc. Natl. Acad. Sci. USA 82, 4394–4398).

A markedly smaller number of unspecific transcripts was obtained with the aid of these vectors, which is why the use of these vectors in transcription reactions has since been described many times. (Goppelt, A., Stelzer, G., Lottspeich, F., Meisterernst, M. (1996) EMBO J. 15, 3105–3115; Kretzschmar, M., Kaiser, K., Lottspeich, F., Meisterernst, M. (1994) Cell 78, 525–534; Meisterernst, M. Roy, A. L., Lieu, H. M. and Roeder, R. G. (1991) Cell 66, 981–993). To the present day, however, the vectors used were exclusively such where the G-free sequence does not exceed a length of 400 nucleotides.

In order to carry out a quantitative and qualitative analysis of the results of the previously described transcription processes, the transcriptions are carried out in the presence of radiolabeled nucleotides and the radiolabeled transcripts are first phenolized and precipitated and then separated on a gel. This causes not only wrongly initiated or wrongly terminated transcripts and unspecifically labeled nucleic acids (for example transcripts or tRNAs caused by the plasmid), but also excess nucleotides, to be removed from the specific transcript. The ratio of the activities of excess radiolabeled nucleotides to radiolabeled transcripts is approximately 10,000:1 under unfavorable conditions, so that the labeled transcript must be concentrated by a factor of approx. 10,000. This concentration of the specific transcript is achieved by the precipitation steps and separation by electrophoresis. However, these concentration steps are unsuitable for automated bulk screening, which is why alternative processes must be developed so as to remove labeled nucleotides in such an extent that quantitative analysis of the transcriptional results are still possible.

The transcription can also be monitored by applying the reaction solution to a membrane, for example a DEAE-cellulose membrane. The radiolabeled transcripts can be detected directly on the membrane. Until now, however, the use of membranes was employed successfully only for detecting transcripts from in-vitro transcriptions which had been carried out in the presence of purified RNA polymerases II (Roeder, R. G. (1974) J. Biol. Chem. 249, 241–248) or purified basal transcription factors (Ohkuma, Y., Sumimoto, H., Horikoshi, M., Roeder, R. G. (1990) Proc. Natl. Acad. Sci. USA 87, 9163–9167). There exists no indication whatsoever that transcripts which are obtained with the aid of concentrated and, if appropriate, pre-purified extracts from cell nuclei, could be detected in this manner.

The exploitation of aspects of transcription in screening active substances was touched upon in WO 96/26959. This publication discloses the sequences of human NFATs (hNFAT) and their potential use in transcription assays which, in turn, are to be employed in a bulk screening, possibly automated, of natural products. In contrast to the transcription process described hereinbelow, however, this assay is a pure binding assay in which no transcription reaction is carried out.

U.S. Pat. No. 5,563,036 describes a further binding assay which can be used for screening substances which can inhibit the binding of transcription factors to nucleic acids. Again, no transcription is carried out in this assay.

U.S. Pat. No. 5,563,039 describes a further example of a binding assay which is also intended to be used for finding substances which can inhibit the binding of in this case a protein which is associated with a tumor necrosis factor receptor (TRADD), to certain DNA sequences.

SUMMARY OF THE INVENTION

Among the objects of the invention, therefore, is the object of overcoming the the problems with prior art systems discussed above. According to this and other objects of the invention, there is provided an in vitro transcription system that is fast, economical and amenable to automation.

According to one aspect of the invention, there is presented a method of identifying a pharmacologically active substance. In one embodiment, this method entails in vitro transcribing a target DNA sequence in the presence of a candidate pharmacologically active agent and determining the amount of labeled transcript, relative to a control.

According to another aspect of the invention, transcription is facilitated by a model promoter. In one embodiment the model promoter comprises the "TATA" box of the human T-cell receptor Vβ8.1, the initiator region of the adenovirus major late promoter, 5 binding sites for the yeast Gal4 protein and, between the "TATA" box and the Gal4 binding sites, at least one unique cleavage site for a restriction endonuclease.

In yet another aspect of the invention, a universal reporter plasmid is a template for transcription. In one embodiment, the universal reporter plasmid contains unique cleavage sites for the restriction endonucleases PstI, EcoRI, SacI, KpnI, SacII, BamHI, SwaI, a model promoter which enables transcription of a G-free target DNA sequence.

In still another aspect of the invention, as transcription system is provided which can be complemented by at least one transcription factor or at least one transcriptional cofactor.

A further aspect of the invention presents automated systems for carrying out the inventive methods.

DETAILED DESCRIPTION OF THE INVENTION

Figure 1:
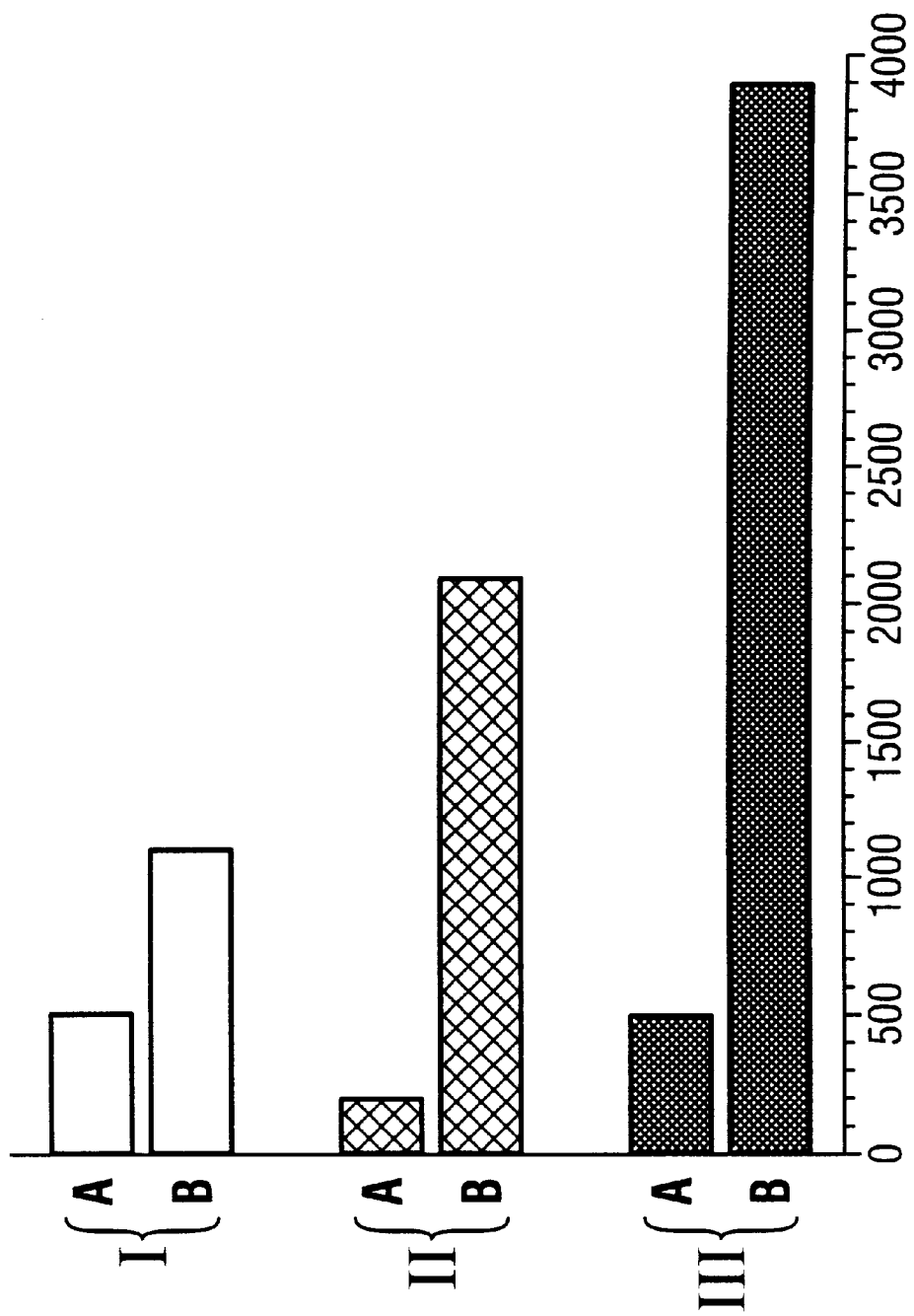
FIG. 1 shows a radioactive read-out of transcription reactions in which various gene-regulatory elements and reporter plasmids having G-free sequences of different lengths were employed.

It is an object of the present invention to provide a process for analyzing the transcription of genes, for example cellular and viral genes, under defined reaction conditions, the process being simple to carry out, reproducible and universally usable in particular for bulk screening.

The invention relates to a process for the cell-free in-vitro transcription of a DNA template which contains a DNA sequence to be transcribed, the sequence being under the control of one or more gene-regulatory elements, and where a) a concentrated and, if appropriate, purified extract of cell nuclei which, if appropriate, can be complemented, or partially or fully replaced, by transcription factors and/or cofactors and at least one labeled nucleotide is used for the transcription, b) after transcription, the proteins which the reaction mixture contains are, if appropriate, isolated and/or subjected to degradation, c) the labeled transcript is bound to a solid matrix, d) the excess labeled nucleotides are removed and e) the amount of labeled transcript is determined.

The process encompasses the actual transcription reaction (a), isolation of the specific transcript (b, c, d) and detection of the specific transcript (e). The process encompasses special embodiments for the isolation of the specific transcript, the abovementioned sequence of b, c and d only being one possibility. The sequence of isolating the specific transcript may also be c, d, b or d, b, c, if appropriate. Furthermore, specific embodiments of the invention can dispense with individual isolation steps. For example, the transcription process may comprise only the steps a, c, d and e or only the steps a, c and e or only a, b, c and e or only a, b, d and e or only a, b and e or only a, d and e.

It is a particular feature of the process that all process steps, i.e. the actual transcription reaction (transcription) and the isolation and detection of the specific transcript can be automated, allowing simple and reliable determination of the amount of specific transcript obtained under the particular reaction conditions, and thus of the transcription rate.

The transcription rate indicates how often a particular gene is transcribed per unit time or, in the transcription process described, how often the DNA sequence to be transcribed is transcribed per unit time. To determine the transcription rate, the amount of radiolabeled transcript obtained after a defined unit time is determined.

An aspect of the process is that transcription is carried out in the presence of activators and/or inhibitors, i.e. in the presence of components which have a positive or negative effect on transcription. For example, an extract from cell nuclei capable of being transcribed can be employed for basal transcription. This basal transcription system can be complemented by activators and/or inhibitors. In comparison with basal transcription, transcription inhibition leads to a reduced transcription rate and thus to a lower amount of specific transcript/unit time, while transcription activation leads to an increased transcription rate and thus to a greater amount of specific transcript/unit time.

The transcription of genes can be divided into several steps—formation of the pre-initiation complex (PIC), PIC activation, initiation, promoter clearance, elongation and termination. In eukaryotes, initiation of transcription requires RNA polymerases (for the transcription of protein-encoding genes, RNA polymerase II) and DNA-binding proteins which allow the specific interaction of RNA polymerase II with the DNA. These DNA-binding proteins are termed transcription factors, the general transcription factors essentially participating in the interaction with the promoter, while the specific transcription factors mediate the action of gene-regulatory elements located downstream or upstream of the promoter.

The general transcription factors TFIIA, TFIIB, TFIID, TFIIE, TFIIF and TFIIH play a role in the transcription of eukaryotic genes. A protein fraction capable of being transcribed which is responsible for a low, basal activity of genes, contains, depending on the promoter, all or most of these general transcription factors and RNA polymerase II (RNA Pol II). A basal activity of the ML promoter is achieved, for example, by TBP (TATA-binding subunit of TFIID), TFIIB, TFIIE, TFIIF, TFIIH and RNA Pol II.

Protein fractions which cause such a basal activity are termed basal transcription systems. For the purposes of the invention, this term is also used for a concentrated and, if appropriate, purified extract from cell nuclei. A transcription carried out with the aid of a basal transcription system is termed basal transcription. Carrying out cell-free transcription in vitro requires at least one basal transcription system, nucleotides and a DNA template to be transcribed.

Activated transcription requires, in addition to the general transcription factors and in addition to a basal transcription system, specific transcription factors and cofactors (accessory proteins) (Kaiser, K., Steizer, G. and Meisterernst, M. (1995) EMBO J. 14, 3520–3527). Specific transcription factors are capable of multiplying the strength of the basal transcription of specific genes, which is only low, and of governing the frequency of transcription initiation. Thus, DNA-binding proteins are highly responsible for how often a gene is transcribed (transcription rate). Other proteins which do not bind directly to the DNA, but which have effects on the activities of transcription factors or RNA polymerases II via protein-protein interactions, such as, for example, cofactors, also play a role in this regulatory process.

An aspect of the process is that a concentrated extract from cell nuclei (nuclear extract from cells, nuclear extract) is employed for the basal transcription. As regards this parameter, the process can be employed universally; this applies to the cell used and also to the eukaryotic species used.

For example, it is possible to obtain concentrated nuclear extracts from cell lines derived from human or animal cells. Cells which are particularly suitable are those which can be grown and propagated in fermenters on a large scale such as, for example, HeLa cells. Furthermore, extracts from the cell nuclei of selected cell types, in particular those which are distinguished by, for example, their cell-type-specific, cell-cycle-specific, development-specific, differentiation-specific or disease-specific make-up with transcription factors and/or cofactors, can be used. In particular, cell types can be used which play a pivotal role in the origin of diseases, such as, for example, cells of the immune system (for example B and T cells).

A special advantage of the process is that it is also possible to isolate and use nuclear extracts from tissues or tumor cells. This is especially advantageous in those cases where no suitable cell line is available. In particular, nuclear extracts can be isolated from readily accessible tissues, such as from animal or human umbilical cords, animal or human transplant waste products, animal or human biopsy material or animal or human tumor tissue (for example tissue removed during surgical procedures) or animal or human placenta, and employed in the process.

An aspect of the process is that concentrated nuclear extracts are prepared by known processes for the purpose of concentrating proteins from the cell nuclei of fresh or frozen cells or from fresh or frozen cell nuclei, for example by a method described by Dignam et al. (Dignam, J. D., Martin, P. L., Shastry, B. S., Roeder, R. G. (1983) Methods in Enzymology 101, 582–598; Dignam, J. D., Lebovitz, R. M., Roeder, R. G. (1983) Nucleic Acid Res. 11, 1475–1489). A special embodiment of the process is that, to prepare a concentrated nuclear extract, processes are used which comprise homogenization of the cell nuclei, followed by dialysis of the homogenate.

An aspect of an important embodiment of the process is that the concentrated extract from cell nuclei is purified by one or more purification steps, in particular simple purification steps, to such an extent that it can be transcribed, i.e. that a specific transcript is obtained when carrying out the process. For example, the extract may be purified by chromatography. Purification can be effected, for example, over nuclear-protein-binding materials such as phosphocellulose, DEAE-cellulose or heparin-Sepharose. Alternatively, cation- and/or anion-exchanger columns or specific affinity columns, for example those where antibodies or oligonucleotides are bound to the column material, may be employed for purification.

An aspect of a special embodiment of the process is that a concentrated nuclear extract is purified over a phosphocellulose column, in particular a P11® column (P11® system, Whatman, Maidstone, England). An aspect of a further special embodiment of the process is that the concentrated nuclear extract is purified by a single step only, for example over a single P11® column, or a single column with column material which contains DEAE-cellulose or heparin-Sepharose.

In a specific embodiment of the P11® purification, the nuclear extract is first bound to the phosphocellulose in the presence of a buffer which, in addition to other constituents, comprises from 0.05 to 0.15 M, preferably 0.1 M, KCl.

Washing of the loaded column with suitable buffers, preferably with a buffer comprising 0.05 to 0.15 M KCl, preferably 0.1 M KCl, leads to unspecific and interfering components being washed from the column. The components which are capable of transcription are preferably eluted from the column in two fractions, first using a buffer comprising, for example, 0.4 to 0.6 M KCl, preferably 0.5 M KCl, followed by a buffer comprising, for example, 0.7 to 1 M KCl, preferably 0.85 M KCl.

A specific embodiment of the process is that the transcription is carried out with the aid of a concentrated, if appropriate purified, nuclear extract in the presence of exogenous RNA polymerase II. The RNA polymerase used can preferably be eukaryotic type II RNA polymerase (RNA polymerase II), in particular animal or human RNA polymerase II.

An aspect of a further embodiment of the process is that a concentrated and, if appropriate, purified nuclear extract is complemented or fully or partially replaced, by addition of proteins, for example transcription factors and/or cofactors (accessory proteins). For example, these proteins can be isolated from cell nuclei, or they can be prepared by recombinant techniques.

A specific embodiment of the process is that the nuclear extract is complemented by a transcription factor and/or cofactor only. In the other extreme, an aspect of the process is that a protein fraction capable of transcription (basal transcription system) is composed exclusively of transcription factors and/or cofactors which have been isolated or which have been prepared by recombinant technology, and of RNA polymerases.

Transcription factors which can be employed are, for example, general and/or specific transcription factors of parts thereof, if appropriate in the form of fusion proteins.

General transcription factors which can be employed are, for example, TFIIA, TFIIB, TFIID, TFIIE, TFIIF, TFIIH, TFIIJ and TBP (TATA-binding protein).

Specific transcription factors which can be used are, for example, NFκB, AP1, NFAT, GATA3, TCF/Lef, CBF, Tat, members of the fos/jun family, of the Oct family (Oct-1, Oct-2) and factors which interact with them, such as, for example, BobI, OCA-B or OBF, of the Ets family, activators of the family of the ATF/CREB proteins, nuclear receptors such as, for example PPARα or the corresponding cell-typespecific iso-forms of transcription factors (Kel, O. V., Romaschenko, A. G., Kel, A. E., Wingender, E., Kolachenov, N. A., (1995) Nucl. Acids. Res. 20, 3–16).

Other examples of specific transcription factors are:
1. Proto-oncogenes, for example jun, fos, ets, myc, bcl-isoforms and erb
2. Hormone receptors, for example (erb), glucocorticoid receptors, estrogen receptors, retinoic acid receptors, vitamin D receptors or
3. Tumor suppressors, for example p53, NF1, WT1, RB
4. Viral pathogens, for example proteins of the herpes simplex virus, such as, for example, VP16 or ICP4, of the papilloma virus, for example E1, E2, E6 or E7, of the adenovirus, such as, for example, E1A or E2A, of the cytomegalovirus, such as, for example, IE86, of the hepatitis B virus, such as, for example, pX, of the HIV virus such as, for example, Tat or Rev
5. Cell-type-specific and/or tissue-specific factors such as, for example, myogenic factors, Pit-1, Oct-2, Pu-1, OCA-B or HNFs or T-cell-specific factors such as Ets-1, GATA3, TCF/Lef, CBF
6. STAT proteins (signal transducers and activators of transcription), for example cytokin-activated transcription factors such as, for example, IL-1 Stat, IL-2 Stat, IL-3 Stat, IL-4, IL-5 Stat, IL-6 Stat, IL-7 Stat, IL-8 Stat, IL-9 Stat, IL-10 Stat, IL-11 Stat, IL-12 Stat ("Stat" means protein which mediates the action) or
7. Proteins which participate in second-messenger transduction cascades, for example CREB or abI,
8. Nuclear receptors, for example second-messenger receptors (for example cAMP or $IP_3$ receptors, $Ca^{2+}$-dependent receptors), retinoic acid receptors, glucocorticoid receptors or steroid receptors,
9. Gene-specific activators or inhibitors, for example specific activators of the IL-2 gene, such as NFκB, AP1 or NFAT
10. Development-specifically, cell-cycle-specifically and differentiation-dependently expressed transcription factors.

Cofactors play a direct or indirect role in transcription, for example via protein-protein interactions and/or protein-DNA interactions. Some cofactors exist already in a basal transcription system, others only in the activated transcription system. Cofactors can have a positive or negative effect on the transcription rate. Cofactors which can be employed are, for example, TBP-associated factors (TAFs), for example $TAF_{II}30$, $TAF_{II}40$, $TAF_{II}55$, $TAF_{II}60$, $TAF_{II}110$, $TAF_{II}150$, $TAF_{II}250$ (Verrijzer, C. P. and Tjian, R. (1996) Trends Biochem. Sci. 21, 338–342; TAFs together with TBP form the TFIID complex, it being possible for the composition of the TAFs in the TFIID to vary considerably);

mediators, i.e. cofactors which are associated with RNA polymerase II, such as, for example, CTD (carboxy-terminal-domain)-interactive proteins and/or repressors and/or activators of RNA polymerase II, in particular RAP 30, RAP 74, RAP 38, SR7 (suppressor of RNA polymerase B, SRB), cyclins or kinases (for example CKII);

general cofactors;

cofactors contained in the USA (upstream stimulatory activity) fraction (Kaiser, K. and Meisterernst, M. (1996) Trends Biochem. Sci., 342–345);

positive cofactors, for example PC1, PC2, PC4 (p15), PC5, PC6, Dr2 (D repressor 2)/PC3, ACF(activating cofactor) CofA (cofactor A), HMG-proteins (chromatin-associated high-mobility group proteins);

negative cofactors, for example NC1, NC2 and/or specific cofactors.

An aspect of the process is that a DNA template is employed for the transcription which comprises one or more gene-regulatory elements and a DNA sequence to be transcribed.

The subject matter of the invention includes a DNA template which can be employed in the above-described process for the cell-free in-vitro transcription. The DNA template comprises one or more gene-regulatory elements and a DNA sequence to be transcribed. The DNA template may additionally comprise further sequence segments.

A gene-regulatory element can be a known gene-regulatory element or a gene-regulatory element to be investigated, or a construct of one or more known gene-regulatory elements and one or more gene-regulatory elements to be investigated.

A gene-regulatory element can comprise any DNA sequences which participate in the gene regulation, or segments thereof. With regard to the gene-regulatory element, the DNA template, or the process, is universal, the gene-regulatory element preferably being derived from a eukaryotic gene, or corresponding to the latter. The gene-regulatory element can be a cellular or viral gene-regulatory element or a synthetic gene-regulatory element. A gene-regulatory element preferably comprises, inter alia, DNA sequences which represent binding sites for DNA-binding proteins (protein-binding DNA sequences, for example binding sites for transcription factors or fusion proteins). A gene-regulatory element can comprise a promoter (promoter sequence) and/or one or more enhancers (enhancer sequence) and/or one or more silencers (silencer sequence). Preferably, the gene-regulatory element can comprise naturally and/or artificially arranged promoter, enhancer and/or silencer sequences or parts thereof.

A promoter can comprise a "TATA" box and/or an initiator region (INR) (initiation of transcription). The promoter can comprise a "GC" box and/or "GAAT" box.

In a specific embodiment of the DNA template, the gene-regulatory element is a model promoter.

A model promoter comprises a promoter and additional protein-binding DNA sequences and, if appropriate, other gene-regulatory elements. The model promoter preferably comprises a "TATA" box and an initiator region. In a specific embodiment, the model promoter comprises the "TATA" box of the human T-cell receptor Vβ8.1 and the initiator region of the ML promoter. These two basal promoter elements allow basal in-vitro transcription. In addition, this specific model promoter has 5 binding sites for the yeast Gal4 protein. The model promoter can be altered as desired, for example with the aid of the methods of molecular biology, for example by complementing the model promoter by, for example, a gene-regulatory element to be investigated, and/or by replacing individual sections of the model promoter by other gene-regulatory elements, for example a gene-regulatory element to be investigated.

To allow manipulation of the model promoter, it contains preferably one or more singular cleavage sites for restriction endonuclease. In a specific embodiment of the model promoter, at least one singular cleavage site for a restriction endonuclease is located between the "TATA" box and the Gal4 binding sites.

In addition to the already existing protein-binding sequences (for example in addition to the Gal4 sequences), other protein-binding sequences can be integrated into the model promoter. This is of particular interest if, for example, other transcription factors to be investigated, for example specific transcription factors, are added in addition to a transcription system that has already been investigated.

An aspect of the process is that fusion proteins can also be employed as transcription activators and/or inhibitors, in combination with the model promoter. Such fusion proteins can be composed, for example, of a DNA-binding domain such as, for example, the DNA-binding domain of the yeast Gal4 protein, and a specific activation domain such as, for example, the activation domain of the HSV activator VP16. Fusion proteins allow defined activators and/or inhibitors, or parts thereof, for example their activation—or inhibition domains, respectively, to be analyzed, without background, for a gene-regulatory element to be investigated. For example, this is possible if the DNA-binding domain is derived from a DNA-binding protein which the transcription system used (for example the concentrated nuclear extract) lacks. For example, the activator (domain), of a transcription factor, which exists as fusion protein with a yeast Gal4 binding domain, can be analyzed without background if concentrated nuclear extracts from mammalian cells are employed in the process, since nuclear extracts from mammalian cells do not contain Gal4.

Gene-regulatory elements and gene-regulatory elements to be investigated which can be used are defined human and/or animal and/or viral gene-regulatory elements, in particular the gene-regulatory elements of genes which are of interest in pathology. Examples are the gene-regulatory elements of the genes of adhesion molecules, growth factors, phosphodiesterases, phosphatases, kinases, ATPases, membrane receptors, second-messenger receptors, hormone receptors, e.g. steroid receptors, metalloproteases, immunophilins, NO-synthases, 5-lipoxygenases, or immunological targets such as the gene-regulatory elements of cytokins, e.g. of interleukins, such as the promoters of T- or B-cell-specifically expressed genes, e.g. of the CD4 receptor, TCR or BCR (T- or B-cell receptors), such as the promoters of lymphoid-specific genes, e.g. of TNF (tumor necrosis factor), or such as the gene-regulatory elements of T-cell-specific retroviruses, e.g. of HTLV-1 or HIV-1.

A special advantage of the process, of the model promoter, is that the gene-regulatory elements which can be used are not only those promoters which contain a "TATA" box such as, for example, the promoter of the gene which encodes interleukin-2 (IL-2) but also promoters which lack a "TATA" box such as, for example, the promoter of the gene which encodes the β-chain of the T-cell receptor. For example, promoters which lack a "TATA" box can be integrated into the model promoter, or into the universal reporter plasmid pGS100, and employed for transcription.

A feature of the DNA sequence to be transcribed is that it lacks one or more nucleobases in this sequence. The DNA sequence to be transcribed preferably comprises, alternatively, either no guanine or no cytosine or no thymine, i.e. the sequence is G-free, C-free or T-free. Furthermore, the sequence may also lack more than one nucleobases, such as guanine and thymine or guanine and cytosine or cytosine and thymine.

G-free, T-free or C-free sequences which are used are, in particular, those where the G-free, T-free or C-free sequence has a length of over 400 nucleotides, preferably between 400 and 2000 nucleotides or longer. In particular, sequences are used which have a length of approximately 500, 600, 700, 800, 900, 1000, 1100, 1200, 1300, 1400, 1500, 1600, 1700, 1800, 1900, 2000, 5000 or more nucleotides. Especially preferred lengths of sequences which lack a specific nucleobase are lengths of approximately 800, 1200, 1600 or 2200 nucleotides.

The DNA template can be a linear or circular DNA sequence, for example the DNA template may be a linear sequence generated by polymerase chain reaction or a plasmid.

In one embodiment, the DNA template is a plasmid and is constructed of all or part of a vector, a model promoter and of a DNA sequence to be transcribed which is, for example, G-free, T-free or C-free.

The object of the invention is a universally utilizable reporter plasmid (universal reporter plasmid). The universal reporter plasmid contains singular cleavage sites for the restriction endonucleases PstI, EcoRI, SacI, KpnI, SacII, BamHI, SwaI, part of the plasmid pUC19, five binding sites for the yeast Gal4 protein, the "TATA" box of the human T-cell receptor Vβ8.1 between the SacII and BamHI restriction sites, the INR (initiator) region of the ML promoter (adenovirus major late promoter) between the BAMHI and SwaI restriction sites, and a G-free sequence with a length of approximately 800 nucleotides (base pairs). The model promoter in the universal reporter plasmid is a synthetic promoter which contains 5 yeast Gal4 binding sites, the singular cleavage sites for PstI, EcoRI, SacI, KpnI, SacII, BamHI and SwaI, the TATA box of the human T-cell receptor Vβ8.1 and the INR of the ML promoter. Any gene-regulatory elements to be investigated can be integrated into this promoter region. Parts of the model promoter or the complete model promoter may be removed and replaced by gene-regulatory elements to be investigated.

Figure 2:
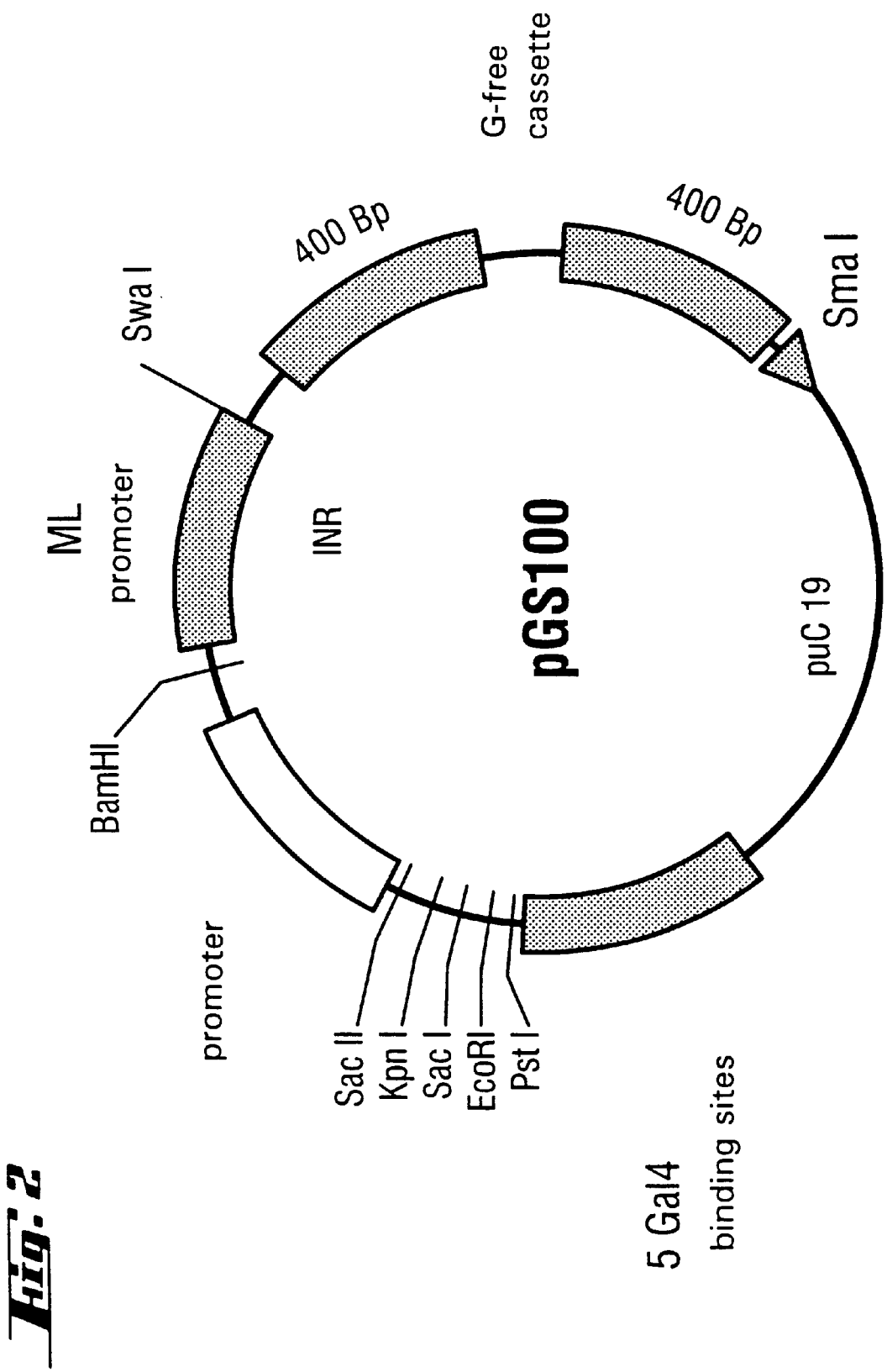
FIG. 2 shows the universal reporter plasmid pGS100.

An embodiment of the universal reporter plasmid is named pGS100 (FIG. 2).

In one embodiment of the universal reporter plasmid pGS100, the synthetic promoter is located in the sequence region between nucleotide positions 2168 and 2337. The initiator region of the adenoviral major late (ML) promoter is located on nucleotide positions 2322 to 2337, and the region with the TATA box of the human T-cell receptor Vβ8.1 promoter on nucleotide positions 2289 to 2316. The five binding sites for the yeast Gal4 protein are located between nucleotide positions 2168 to 2260.

A further embodiment of the universal reporter plasmid pGS100 is shown by the nucleotide sequence SEQ ID NO. 1.

A further embodiment of the universal reporter plasmid pGS100 was deposited at the DSMZ-Deutsche Sammlung von Mikroorganismen und Zellkulturen GmbH, Mascheroder Weg 1b, D-38124 Braunschweig, in compliance with the provisions of the Budapest Treaty on the international recognition of the deposit of microorganisms for the purposes of patent procedure; DSM deposit number: 11450.

An aspect of the process is that proteins which directly or indirectly interfere with detection of the specific transcript in such a way that unambiguous detection of the specific transcript is no longer possible, are eliminated and/or subjected to degradation after transcription. Elimination or degradation comprises, in particular, process steps which are simple to carry out such as, for example, those where the reaction is quenched by a chemical and/or mechanical and/or enzymatic process step and, if appropriate, the transcripts are simultaneously freed from interfering proteins in such a way that excess labeled nucleotides can be eliminated from the specific transcripts after this process step, for example by washing steps.

An aspect of this embodiment of the process is that, for example, the proteins can be subjected to degradation with the aid of proteases after the transcription reaction. Proteases which can be employed are, for example, zinc proteases, serine proteases, thiol proteases and carboxyproteases. Proteinase K, trypsin, chymotrypsin, carboxypeptidase A, papain and pepsin can be employed, in particular. A special embodiment of the process is that a digestion with proteinase K is carried out after transcription.

To be able to determine the extent of the transcription, i.e. the transcription rate, the amount of specific transcript must be determined.

An aspect of the process is that the transcription is carried out in the presence of labeled nucleotides or that the specific transcript is labeled. For example, the transcript can be non-radiolabeled if suitable non-radiolabeled nucleotides are employed for the transcription. Labeling groups for nucleotides which can be used are, for example, fluorescent groups such as dansyl (=N-dimethyl-1-aminonaphthyl-5-sulfonyl) derivatives, fluorescein derivatives or coumarin derivatives, or chemiluminescent groups such as acridine derivatives. The abovementioned labeling groups allow direct detection of the specific transcript. In addition, it is also possible to use labeling groups which are suitable for indirect detection of the transcript. Examples are digoxygenin, which can be detected with specific anti-digoxigenin-antibodies, for example in an ELISA, biotin, which can be detected via the biotin/avidin system, and linker arms containing functional groups, which allow subsequent derivatization with a detectable reporter group. An example of the last-mentioned possibility is, for example, an aminoalkyl linker which, after transcription, can be reacted, and detected, with an acridinium activated-ester in the chemiluminescence test.

A special embodiment of the process is to carry out the transcription in the presence of radiolabeled nucleotides. The nucleotides can be radiolabeled, for example, with phosphorus ($^{32}$P or $^{33}$P), sulfur ($^{35}$S) or tritium ($^{3}$H).

A special embodiment of the process is that the specific transcripts are isolated from the reaction mixture by binding to a solid phase (solid matrix), for example by binding to a microtiter plate or by binding the specific transcript to special filters, membranes or other solid phases, in particular by binding to a charged membrane or a charged filter, preferably made of nylon or nitrocellulose, especially preferably by binding to a membrane which contains charged groups such as, for example, diethylaminoethyl groups, such as, for example, a DEAE-cellulose membrane. An aspect of this embodiment is that the specific transcripts which are bound to the solid matrix can be freed from excess labeled nucleotides by means of washing steps to such an extent that unambiguous detection of the specific transcript is possible.

In comparison with the conventional isolation and detection, consisting of phenolization, precipitation and subsequent separation of the transcript on a denaturing gel, this process, surprisingly, yields specific signals which can be detected equally unambiguously (cf. Example 7 and FIG. 4).

The process is suitable for generating specific signals triggered, for example, by the specific transcription in the presence of, for example, an activator (activator transcription) or of an inhibitor (inhibitor transcription) the signals differing from the basal signal strength, triggered by the basal transcription, for example in the absence of activator or inhibitor, by at least a factor of 7, preferably by a factor of 8, in particular cases even by a factor of 9 or 10 (cf. Example 7 and FIG. 4).

An important embodiment of the process is that it can be employed for screening pharmacologically active substances. To test candidate pharmacologically active substances for their activity (e.g. activating or inhibiting property), the transcription is carried out in the presence of the active substance to be tested. If appropriate, individual components, e.g. the concentrated nuclear extract, can be preincubated with the active substance to be tested. In addition, specificity of the active substance to be tested can be characterized by carrying out the transcription in the presence of the active substance to be tested in parallel in a plurality of transcription reaction mixtures, each reaction mixture comprising different components, and then determining and comparing the transcription rates.

Examples of active substances to be tested can be natural products and/or substances from chemical and combinatory substance libraries. Natural products can be isolated, for example, from plants, animals, plant secretions, animal secretions and, in particular, from microorganisms such as, for example, from fungi, yeasts, bacteria or algae.

Another special embodiment of the process is that the transcription is carried out in the presence of an active substance, transcription factor, cofactor or cell-type-specific nuclear extract to be tested and a parallel reaction mixture is performed in the absence of the active substance, transcription factor, cofactor or cell-type-specific nuclear extract to be tested, but otherwise under identical conditions, and the activity (e.g. inhibitory, activating) or the effect of the active substance, transcription factor, cofactor or cell-type-specific nuclear extract to be tested in relation to a gene-regulatory element (or gene) and/or an transcription factor and/or cofactor is determined from the difference in the amounts of labeled transcript.

An aspect of the process is that the effect of a protein participating in gene regulation and to be investigated is determined with the aid of transcriptions carried out in parallel under identical conditions, the protein to be investigated only being present in one of the two reaction mixtures.

An aspect of one embodiment of the process is that a) at least two transcriptions are carried out in parallel under identical conditions, where b) the transcription reaction mixtures differ only by the fact that they comprise differing amounts of the active substance to be tested and/or at least one transcription factor and/or at least one cofactor and/or a concentrated nuclear extract, c) the resulting amount of labeled transcript is determined for each reaction mixture after transcription, and d) the activity and/or specificity of the active substance, transcription factor, cofactor and/or concentrated nuclear extract to be tested in relation to the gene-regulatory element is determined from the difference in the resulting amounts of labeled transcript.

This process allows the effect of each individual component (for example on the nuclear extract (i.e. on a specific cell type) or on a specific transcription factor) which the transcription reaction mixture contains, to be tested target-specifically. For example the effect of an active substance to be investigated on a defined gene-regulatory element can be analyzed. What is decisive here is that the reaction conditions of the transcription can be defined accurately.

The process provides a way of influencing in a target-specific manner the action of individual factors on pathological gene expression since suitable reaction conditions can be adjusted or set accurately by selecting the gene-regulatory element and the transcription factors and/or cofactors and/or cell-type-specific nuclear extracts.

A particular advantage of the process is that it allows the identification of pharmacologically active substances which are capable of exerting positive or negative effects on the transcription under defined conditions, in particular those active substances which activate or inhibit the transcription of defined (target) genes, these active substances having a specific effect on defined gene-regulatory elements and/or defined transcription factors, cofactors and/or cell-type-specific nuclear extracts (or cells).

The invention relates to the use of the process for the identification of specific active substances. The process can for example be used to characterize the substance to be tested. The process can for example be used to characterize a substance to be tested with respect to its specificity under defined conditions. A pharmaceutically active substance identified by the process should for example inhibit or activate the transcription of the DNA-sequence which is under control of the gene regulatory element.

A further, especially advantageous characteristic of the process is that all steps can be automated in a simple manner. For example, the pipetting robot Biomek 2000® (Beckman, Munich), connected to a supply robot module, can be employed. The transcripts which are bound to a solid phase can then be washed manually or automatically, for example with the aid of a conveyor belt.

An aspect of the present invention provides that a pipetting robot, for example Biomek 2000®, is equipped with the individual reaction components, such as protein fraction (e.g. nuclear extract and other proteins), DNA template, transcription buffer, substances to be investigated in transcription, pipette tips, microtiter plates and membranes. The individual reactions are composed of these components, for example in the wells of microtiter plates, all pipetting steps being carried out automatically. In this manner, 96 or more different transcription reaction mixtures per plate can be dealt with simultaneously, combined with small sample volumes, in particular volumes of less than 100 $\mu$l, preferably 10 to 50 $\mu$l, in particular 20 $\mu$l. Each transcription takes approximately 1 to 1.5 hours, so that up to 1000 or more transcriptions can be carried out per day in this manner when the incubation times are utilized in the best possible fashion.

The transcription can be carried out for example at temperatures of 20–50° C. Carrying out the transcription at approximately 30° C. is especially preferred.

Since in particular the active substances, transcription factors, cofactors to be tested and, if appropriate, also the concentrated nuclear extracts to be tested are only available in small amounts, but these substances should be tested under a variety of reaction conditions in a large number of transcriptions, the process must meet the requirement that the sample volumes required for the transcription reaction be as small as possible. It is therefore of particular importance that this process is also suitable for being carried out on a nanoliter scale, i.e. reaction volumes of approx. 50–500 nl.

The transcription process can be employed universally. It can be used for identifying and characterizing gene-regulatory elements (i.e. a specific gene as target), of transcription and/or cofactors and/or other proteins which play a direct or indirect role in the regulation of gene transcription (i.e. a specific protein as target) and/or of concentrated nuclear extracts (i.e. a specific nuclear extract or a specific cell type as target). In particular, the transcription process can be utilized for identifying novel gene-regulatory elements which are of interest in pathology and for the assignment of gene-regulatory proteins which mediate the effect of these elements to the corresponding gene-regulatory elements.

In comparison with cellular assays, the above-described transcription process has a higher target specificity. In contrast to cellular assays, the cellular uptake of individual components has no effect on the efficacy of the transcription.

In addition, the above-described process can be carried out simply and rapidly (for example, the individual components can be prepared and stored frozen). The process is simple to standardize and can be employed universally, since it can be applied to virtually any cell type and any gene.

The process allows the identification of pharmacologically active substances which can be used for the preparation of pharmaceuticals. Active substances identified by these transcription processes should cause considerably less side-effects, compared with known active substances. For example, it is possible to test, or identify, active substances which can be employed for the preparation of pharmaceuticals for the treatment of (auto)immune diseases, metabolic diseases, cancer, cardiovascular diseases, communicable diseases, rheumatism, diabetes, degenerative and mental diseases, in particular for the preparation of pharmaceuticals for the treatment of rheumatoid arthritis, multiple sclerosis, diabetes mellitus, allergies, asthma, anaphylaxis, atopic dermatitis, Alzheimer's disease, Parkinson's disease, AIDS, Creutzfeldt-Jakob disease, epilepsy, schizophrenia, arteriosclerosis and tuberculosis.

In addition, this universal process offers a large number of other possible uses. For example, the process can be employed analogously in animal pathology and animal breeding, in crop protection or in plant breeding for finding specific, pharmacologically active substances if the relevant basal transcription systems from the organisms in question and the specific gene-regulatory elements, transcription factors and/or cofactors and/or other proteins which participate directly or indirectly in the transcription reaction.

In principle, this in-vitro transcription process can also be utilized analogously for the identification of substances which may be used in the preservation of materials and of foodstuffs if, correspondingly, the gene-regulatory elements, systems capable of transcription, transcription factors and/or cofactors of microorganisms, for example of yeasts, fungi, bacteria or of insects are used.

EXAMPLES

Example 1

Preparation of HeLa Nuclear Extracts

The nuclear extracts are prepared starting from HeLa cell nuclei. HeLa cell nuclei are commercially available from various companies (for example "4° C.", Mons; Sigma, Munich, Santa Cruz Biotechnology, Heidelberg). Processing of the cell nuclei which is described hereinbelow is effected at 4° C. (cold room). The buffers are adjusted with Tris pH 6.8 at room temperature (RT) which corresponds to pH 7.3 at 4° C. Prior to use, the buffers are treated with DTT (stock solution 1 M in water) to an end concentration of 5 mM and PMSF (stock solution 200 mM in DMSO) to an end concentration of 1 mM.

Processing of the cell nuclei comprises the following steps:

1. Defrost cell nuclei on ice and determine NPV volume (nuclear pellet volume).
2. Into two different glass beakers, introduce in each case 1/2 NPV volume of 0.02 M KCl buffer (buffer with low salt content: 20 ml 1 M Tris pH 6.8 RT, 250 ml 100% glycerol, 6.67 ml 3 M KCl, 1.5 ml 1M $MgCl_2$ 0.4 ml 0.5 M EDTA, $H_2O$ to 1000 ml) and 1.2 M KCl buffer (buffer with high salt content: 20 ml 1 M Tris pH 6.8 RT, 250 ml 100% glycerol, 400 ml 3 M KCl, 1.5 ml 1 M $MgCl_2$ 0.4 ml 0.5 M EDTA, $H_2O$ to 1000 ml), respectively.

Each buffer is treated with 0.0007×NPV/2$\beta$-mercaptoethanol and 0.001×NPV/2 0.2 M PMSF.

The pellet is resuspended in 1/2 volume 0.02 M KCl buffer and gently homogenized using a pestle (6×).

3. Introduce homogenate into glass beaker and treat dropwise with 1.2 M KCl buffer with continuous stirring in the course of 30 minutes. After a further 30 minutes' stirring, the extraction is finished. Spin off (Beckman centrifuge, SS34 rotor at 14,000 rpm, 30 min, 4° C.), further process pellet and supernatant separately.
4. Dialyze supernatant in buffer 1 (40 ml 1 M Tris pH 6.8 RT, 400 ml glycerol, 0.8 ml 0.5 M EDTA, $H_2O$ to 2000 ml) until the conductivity of buffer 2 is reached (40 ml 1 M Tris pH 6.8 RT, 400 ml glycerol, 0.8 ml 0.5 M EDTA, 66.7 ml 3 M KCl, $H_2O$ to 2000 ml) (45–55 min).
5. Spin off dialyzed supernatant (Beckman, SS34 rotor, 18,000 rpm, 20 min, 4° C.). The HeLa nuclear extract is in the supernatant (HeLa nuclear extract=HeLa NE). Aliquots of the extract are frozen in liquid $N_2$. Transfer pellet from nuclear extraction into homogenizer, treat with 10 ml of TGME/5 mM DTT (TGME for 1l: 250 ml 100% glycerol, 50 ml Tris pH 7.3 RT, 5 ml 1 M $MgCl_2$, 0.2 ml 500 mM EDTA pH 8.0), homogenize (vigorously) 20× with a pestle and freeze in liquid $N_2$ (HeLa nuclear pellet).

Example 2
Preparation of the Phosphocellulose Column for Isolating the Nuclear Extract
1. Repeatedly wash P11® column material in water. Determine volume of swollen material.
2. Add 5 volumes of 0.5 N NaOH, leave to stand for 5 minutes, then immediately filter with suction through a folded filter.
3. Wash with water to pH 11.
4. Add 25 volumes of 0.5 N HCl. Leave to stand for 5 minutes, then immediately filter with suction.
5. Wash with water to pH 3.
6. Wash with 1 M Tris pH 7 until pH constant at 7. Store column material at 4° C. Equilibrate, best overnight.

Example 3
Chromatographic Purification of the Nuclear Extract by Phosphocellulose Chromatography
The capacity of the P11® material is 10 mg protein/1 ml material.
Chromatography is effected as follows:
1. Pack column with P11® material and equilibrate in buffer 2 (with freshly added DTT and PMSF, see Example 1). Attach column to pump.
2. Load (with 1 column volume (CV)/h) nuclear extract (in buffer 2).
3. Wash column with 5 CV buffer 2 (5–10 CV/h).
4. Elute with buffer 3 (40 ml 1 M Tris pH 6.8 RT, 400 ml glycerol, 0.8 ml 0.5 M EDTA, 200 ml 3 M KCl, $H_2O$ to 2000 ml; 2 CV/h). After no more protein is eluted, run through a further 2 CV buffer 3.
5. Elute with buffer 4 (40 ml 1 M Tris pH 6.8 RT, 400 ml glycerol, 0.8 ml 0.5 M EDTA, 333 ml 3 M KCl, $H_2O$ to 2000 ml; 2 CV/h) and collect peak fractions.
6. Elute with buffer 5 (40 ml 1 M Tris pH 6.8 RT, 400 ml glycerol, 0.8 ml 0.5 M EDTA, 567 ml 3 M KCl, $H_2O$ to 2000 ml; 2 CV/h) and collect peak fractions.
7. Dialyze each of the 2 eluates against buffer 2 until the conductivity is constant and then freeze aliquots in liquid $N_2$.

Example 4
Standard Transcription Process Using a Polyacrylamide Gel for Separating the Transcripts
A transcription reaction mixture (end volume 20 µl) may consist of the following components:

a) general transcription factors in the form of pre-purified nuclear extracts or produced by recombinant technology, if appropriate complemented by further specific transcription factors, activators, inhibitors or fusion proteins;
b) DNA template (for example vector pGS100 with gene-regulatory element to be investigated);
c) transcription buffer comprising, for example, the active substance to be investigated;
d) labeled and unlabeled nucleotides;
re a) buffer 4 eluate and buffer 5 eluate (of Example 3) are contained in the nuclear extract capable of transcription (all general transcription factors). The optimal amounts of buffer 4 eluate and buffer 5 eluate must be determined for each individual preparation (approx. 3 µl of buffer 4 eluate and 2 µl of buffer 5 eluate per reaction mixture);
re b) 100 ng of DNA template (gene-regulatory element in the reporter plasmid, for example in pGS100) are normally employed per reaction mixture;
re c) transcription buffer (5 mM $MgCl_2$, 25 mM HEPES KOH pH 8.2, 0.5 µl BSA acetylated (stock 20 mg/ml), approx. 10% glycerol, approx. 70 mM KCl, 0.2 mM PMSF, 10 mM DTT) plus in each case 20 U RNase inhibitor per reaction mixture;
re d) NTPs (ATP, UTP in each case 100 µM end concentration, CTP 5 µM end concentration, o-m-GTP 20 µM end concentration, $\alpha$-$^{32}$P-CTP approx. 0.12 µM end concentration 3000 Ci/mmol, 10 mCi/ml).
1. The transcription buffer and the dNTPs are introduced and the DNA template is added.
2. Transcription activator and buffer 4 eluate and buffer 5 eluate are added.
3. To carry out the transcription reaction, incubate for 1 h at 30° C.
4. Addition of 400 µl of stopmix (7M urea, 10 mM Tris HCl pH 7.8, 10 mM EDTA/NaOH pH 8, 0.5% SDS, 100 mM LiCl, 100 µg/ml tRNA, 300 mM Na acetate) and 400 µl of phenol/chloroform/isoamyl alcohol (25/24/1). Mix and spin (SS34 rotor, Beckman centrifuge, 5 min, 14,000 rpm, RT). Draw off supernatant, add 400 µl of isopropanol and mix, then incubate for 1 h at −20° C.
5. Spin (SS34 rotor, Beckman centrifuge, 14,000 rpm, 30 min, 4° C.), wash pellet in 70% ethanol and then dry in a Speedvac.
6. Take up pellet in 10 µl loading buffer (955 µl 100% formamide (deionized), 10 µl 0.5 M EDTA, 20 µl 1 M Tris pH 7, in each case 0.003% bromophenol blue/xylene cyanole, $H_2O$ to 1 ml) and incubate for 15 minutes at 50° C.
7. Separation of the transcript in a 5% strength denaturing polyacrylamide gel with 1×TBE as running buffer. Forerun 20 min at 60 mA. Load gel. Run gel for approx. 1 hour at 60 mA.
8. Fix gel in 10% acetic acid, dry, and, in a Phosphoimager®, expose to an X-ray film.

Example 5
Protocol for in-vitro Transcription which can be Automated Using a Filter for Binding the Transcript
1. The transcription buffer and the dNTPs are introduced and the DNA template is added.
2. Buffer 4 eluate and buffer 5 eluate and, if appropriate, transcription activator or transcription inhibitor are added.
3. The mixture is incubated for 1 hour at 30° C. to perform the transcription reaction.
4. Addition of 5 µl proteinase K mix (1 µl proteinase K solution [20 mg/ml], 1 µl 10% SDS, 0.5 µl 0.5 M EDTA pH 8, 1 µl 50 mM Tris pH 7.8, $H_2O$ to 5 µl).
5. Incubate for 15 min at 30° C.

6. Briefly wash DEAE membrane NA 45® (Schleicher und Schuell) in membrane washing buffer (100 mM sodium phosphate buffer pH 7.5, 250 mM NaCl, 2% sodium pyrophosphate).
7. From this reaction mixture, pipette 5 µl onto the membrane and allow to dry for 5 minutes.
8. Gently shake membrane for 4×15 minutes in approx. 100 ml of membrane washing buffer (+1% Triton).
9. Transfer membrane onto Whatmann 3 MM® paper (Whatman, Maidstone, England), dry in the air, cover with film and expose the filters to an X-ray film using a Phoshoimager®.

Example 6

Following the in-vitro Transcription Process Using a Filter, the Transcription Reaction is Carried out in Parallel with Three Different Reporter Plasmids The procedure is as described in Examples 1 to 3 and 5. The reporter plasmids used are pMRG5 (TATA box of the HIV promoter, initiator region of the ML promoter and a G-free cassette approximately 400 nucleotides in length in pUC 19 (Kretschmar, M., Kaiser, K., Lottspeich, F., Meisterernst, M. (1994) Cell. 78, 525–534), pGS100 (FIG. 2) and pVβML (constructed like pGS100, but contains only a 400 bp G-free cassette instead of the 800 bp G-free cassette). In each case 100 ng DNA template and 3 µl of the P11® fractions (buffer 4 eluate and buffer 5 eluate) are employed for the transcription reactions. The reactions are carried out in each case in parallel without and with activator (fusion protein composed of Gal4 binding domain and a polyglutamine activation domain). The results are shown and explained in FIG. 1.

Example 7

Comparison of the Signal Strength (as a Measure of the Amount of Transcript and thus the Transcription Strength) of the Radiolabeled Transcripts Obtained in a Standard Transcription Process with Those Obtained with the Above-described in-vitro Transcription Process The transcription reactions are carried out as described in Examples 1 to 5 and parallel reaction mixtures are analyzed in the filter assay (Example 5) or gel assay (Example 4). In each case 200 ng of pMRG5 are employed as the DNA template for the reactions. Some transcription reactions are carried out in the presence of 30 ng Gal4-VP16, which is employed as activator. The results are shown and described in FIG. 3.

Example 8

Summary

The data are further explained with reference to the more detailed description of the figures presented below.

FIG. 1: Radioactive read-out of transcription reactions in which various gene-regulatory elements and reporter plasmids having G-free sequences of different lengths were employed.

What is shown is a comparison of two standard promoters with the universal reporter plasmid pGS100 (FIG. 2). The transcription reaction was carried out as described in Example 6.
A) Basal transcription: Amount of radioactive transcript [in relative units] obtained without activation of the promoter (basal signal strength);
B) Activated transcription: Amount of radioactive transcript [in relative units] obtained with activation of the promoter with Gal4-polyglutamine.
I) The reporter plasmid used was pMRG5 (Kretschmar, M., Kaiser, K., Lottspeich, F., Meisterernst, M. (1994) Cell 78, 525–534). The synthetic promoter in pMRG5 contains the TATA box of the HIV promoter, the initiator of the ML promoter and a G-free sequence approximately 400 nucleotides in length in pUC19.
II) The reporter plasmid used was pVβML. The construction of the reporter plasmid pVβML is as for the reporter plasmid pGS100, but it contains a G-free sequence of only 400 nucleotides in length instead of the 800 nucleotides.
III) The reporter plasmid used was pGS100, which contains a G-free sequence of approximately 800 nucleotides.

What was compared in each case was the basal (A) and the activated transcription (B). The activator employed was a fusion protein consisting of a Gal4 binding domain (94 amino-terminal amino acids) and a polyglutamine activation domain (synthetic peptide of 11 glutamic acid units). The data plotted are the absolute values (in relative units as they are obtained with the aid of a phosphoimager) after deducting the background. In the transcription reactions, in which pGS100 was used as the reporter plasmid, both higher absolute values and, due to the differing construction of the synthetic promoters, an activability which is superior to mRG5, were measured. In addition, the positive effect of a G-free sequence which has a length of over 400 nucleotides is apparent.

FIG. 2: Universal reporter plasmid pGS100.

The universal reporter plasmid pGS100 contains a synthetic promoter region as model promoter upstream of a G-free region, approximately 800 base pairs in length, in pUC19. Within the BamHI and SwaI restriction sites there is located the initiator region of the adenoviral major late (ML) promoter. Between the SacII and BamHI restriction sites, there is located the region with the TATA box of the human T-cell receptor Vβ8.1 promoter. These two basal promoter elements (initiator and TATA box) allow the basal transcription in vitro. Since these candidate target genes may be of specific importance for screening, it is possible to exchange them individually for the corresponding regions of the genes to be investigated (corresponding gene-regulatory elements). Any regulatory regions of target genes may be introduced into the polylinker downstream of the basal promoter (specific activation). Alternatively, the entire promoter region may be exchanged. Upstream of the polylinker (SacII to PstI), pGS100 contains five binding sites for the yeast Gal4 protein. This also allows the analysis of synthetic transcription activators, for example fusion proteins composed of any desired activation domain (e.g. of the herpes simplex transactivator VP16) and of a Gal4 DNA binding domain. The G-free sequence is an essential unit of pGS100.

Figure 3:
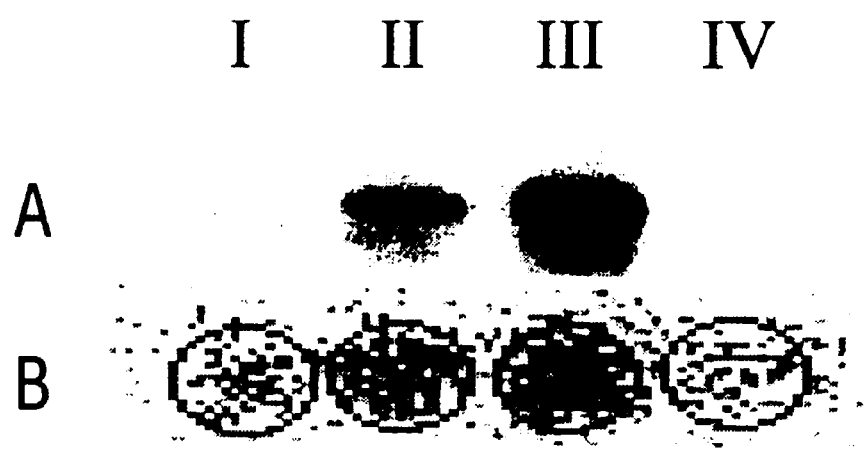
FIG. 3 shows a comparison of the efficacy of a conventional standard transcription process with the above-described cell-free in-vitro transcription process.

FIG. 3: Comparison of the efficacy of a conventional standard transcription process with the above-described cell-free in-vitro transcription process.

FIG. 3 shows a comparison of the signal strengths (as a measure of the amount of transcript and thus of the transcription strength) which are obtained under different reaction conditions. The transcription reactions are carried out as described in Example 7.
A) Conventional standard transcription process, in which the specific transcripts are freed from proteins and excess nucleotides by phenol treatment, precipitation with ethanol and subsequent denaturing gel electrophoresis;
B) above-described in-vitro transcription process, in which the proteins are digested with proteinase K and the excess nucleotides are removed by washing of the specific transcripts which are bound to DEAE filters;
I) The material employed for the transcription is an extract from HeLa cell nuclei which is capable of transcription and which has been purified over a P11® column, without the corresponding DNA template (control experiment);

II) basal transcription: a reaction mixture which corresponds to the reaction mixture of I is treated with the reporter plasmid pMRG5 as the DNA template and the transcription reaction is carried out; the basal signal strength is determined in this manner;

III) activated transcription: a reaction mixture which corresponds to the reaction mixture II is additionally treated with the transcription activator, a fusion protein composed of the DNA binding domain of Gal4 and the activation domain of VP16 (Gal4-VP16), and the transcription is carried out; in this manner, the activated signal strength is obtained;

IV) a reaction mixture corresponding to the transcription reaction mixture of III was treated with α-amanitin as RNA polymerase II inhibitor (control experiment).

A comparison of the signal strengths which were obtained with the two different processes under the different reaction conditions shows that not only the basal (II), but also the activated (III), transcription using the in-vitro transcription process described herein can be measured, the signal strengths being similar to those which are obtained when a conventional transcription process is used.

The fact that even the basal signal strength can be measured is of utmost importance so that the above-described transcription process can also be employed for screening transcription inhibitors. An approximately 8-fold decrease in the signal is achieved with the aid of the specific RNA polymerase II inhibitor α-amanitin (comparisons III and IV).

The foregoing detailed description and examples are presented solely by way of illustration and are not meant to be limiting. Thus, it will be aparent to the artisan practicing the invention that it will be subject to modification without departing from the sprit of the invention.

German Application Number 19710159.3, filed Mar. 12, 1997 is hereby incorporated by reference in its entirety.

All of the foregoing references cited herein are also hereby incorporated by reference.

TABLE 1

SEQ ID NO. 1

| | | | | | |
|---|---|---|---|---|---|
| TTTCCTGTGT | GAAATTGTTA | TCCGCTCACA | ATTCCACACA | ACATACGAGC | CGGAAGCATA | 60 |
| AAGTGTAAAG | CCTGGGGTGC | CTAATGAGTG | AGCTAACTCA | CATTAATTGC | GTTGCGCTCA | 120 |
| CTGCCCGCTT | TCCAGTCGGG | AAACCTGTCG | TGCCAGCTGC | ATTAATGAAT | CGGCCAACGC | 180 |
| GCGGGGAGAG | GCGGTTTGCG | TATTGGGCGC | TCTTCCGCTT | CCTCGCTCAC | TGACTCGCTG | 240 |
| CGCTCGGTCG | TTCGGCTGCG | GCGAGCGGTA | TCAGCTCACT | CAAAGGCGGT | AATACGGTTA | 300 |
| TCCACAGAAT | CAGGGGATAA | CGCAGGAAAG | AACATGTGAG | CAAAAGGCCA | GCAAAAGGCC | 360 |
| AGGAACCGTA | AAAAGGCCGC | GTTGCTGGCG | TTTTTCCATA | GGCTCCGCCC | CCCTGACGAG | 420 |
| CATCACAAAA | ATCGACGCTC | AAGTCAGAGG | TGGCGAAACC | CGACAGGACT | ATAAAGATAC | 480 |
| CAGGCGTTTC | CCCCTGGAAG | CTCCCTCGTG | CGCTCTCCTG | TTCCGACCCT | GCCGCTTACC | 540 |
| GGATACCTGT | CCGCCTTTCT | CCCTTCGGGA | AGCGTGGCGC | TTTCTCAATG | CTCACGCTGT | 600 |
| AGGTATCTCA | GTTCGGTGTA | GGTCGTTCGC | TCCAAGCTGG | GCTGTGTGCA | CGAACCCCCC | 660 |
| GTTCAGCCCG | ACCGCTGCGC | CTTATCCGGT | AACTATCGTC | TTGAGTCCAA | CCCGGTAAGA | 720 |
| CACGACTTAT | CGCCACTGGC | AGCAGCCACT | GGTAACAGGA | TTAGCAGAGC | GAGGTATGTA | 780 |
| GGCGGTGCTA | CAGAGTTCTT | GAAGTGGTGG | CCTAACTACG | GCTACACTAG | AAGGACAGTA | 840 |
| TTTGGTATCT | GCGCTCTGCT | GAAGCCAGTT | ACCTTCGGAA | AAAGAGTTGG | TAGCTCTTGA | 900 |
| TCCGGCAAAC | AAACCACCGC | TGGTAGCGGT | GGTTTTTTTG | TTTGCAAGCA | GCAGATTACG | 960 |
| CGCAGAAAAA | AAGGATCTCA | AGAAGATCCT | TTGATCTTTT | CTACGGGGTC | TGACGCTCAG | 1020 |
| TGGAACGAAA | ACTCACGTTA | AGGGATTTTG | GTCATGAGAT | TATCAAAAAG | GATCTTCACC | 1080 |
| TAGATCCTTT | TAAATTAAAA | ATGAAGTTTT | AAATCAATCT | AAAGTATATA | TGAGTAAACT | 1140 |
| TGGTCTGACA | GTTACCAATG | CTTAATCAGT | GAGGCACCTA | TCTCAGCGAT | CTGTCTATTT | 1200 |
| CGTTCATCCA | TAGTTGCCTG | ACTCCCCGTC | GTGTAGATAA | CTACGATACG | GGAGGGCTTA | 1260 |
| CCATCTGGCC | CCAGTGCTGC | AATGATACCG | CGAGACCCAC | GCTCACCGGC | TCCAGATTTA | 1320 |
| TCAGCAATAA | ACCAGCCAGC | CGGAAGGGCC | GAGCGCAGAA | GTGGTCCTGC | AACTTTATCC | 1380 |
| GCCTCCATCC | AGTCTATTAA | TTGTTGCCGG | GAAGCTAGAG | TAAGTAGTTC | GCCAGTTAAT | 1440 |
| AGTTTGCGCA | ACGTTGTTGC | CATTGCTACA | GGCATCGTGG | TGTCACGCTC | GTCGTTTGGT | 1500 |
| ATGGCTTCAT | TCAGCTCCGG | TTCCCAACGA | TCAAGGCGAG | TTACATGATC | CCCCATGTTG | 1560 |

TABLE 1-continued

SEQ ID NO. 1

| | | | | | |
|---|---|---|---|---|---|
| TGCAAAAAAG | CGGTTAGCTC | CTTCGGTCCT | CCGATCGTTG | TCAGAAGTAA | GTTGGCCGCA 1620 |
| GTGTTATCAC | TCATGGTTAT | GGCAGCACTG | CATAATTCTC | TTACTGTCAT | GCCATCCGTA 1680 |
| AGATGCTTTT | CTGTGACTGG | TGAGTACTCA | ACCAAGTCAT | TCTGAGAATA | GTGTATGCGG 1740 |
| CGACCGAGTT | GCTCTTGCCC | GGCGTCAATA | CGGGATAATA | CCGCGCCACA | TAGCAGAACT 1800 |
| TTAAAAGTGC | TCATCATTGG | AAAACGTTCT | TCGGGGCGAA | AACTCTCAAG | GATCTTACCG 1860 |
| CTGTTGAGAT | CCAGTTCGAT | GTAACCCACT | CGTGCACCCA | ACTGATCTTC | AGCATCTTTT 1920 |
| ACTTTCACCA | GCGTTTCTGG | GTGAGCAAAA | ACAGGAAGGC | AAAATGCCGC | AAAAAAGGGA 1980 |
| ATAAGGGCGA | CACGGAAATG | TTGAATACTC | ATACTCTTCC | TTTTTCAATA | TTATTGAAGC 2040 |
| ATTTATCAGG | GTTATTGTCT | CATGAGCGGA | TACATATTTG | AATGTATTTA | GAAAAATAAA 2100 |
| CAAATAGGGG | TTCCGCGCAC | ATTTCCCCGA | AAAGTGCCAC | CTGGGGGACT | AGAGTCTCCG 2160 |
| CTCGGAGGAC | AGTACTCCGC | TCGGAGGACA | GTACTCCGCT | CGGAGGACAG | TACTCCGCTC 2220 |
| GGAGGACAGT | ACTCCGCTCG | GAGGACAGTA | CTCCGACCTG | CAGGAATTCG | AGCTCGGTAC 2280 |
| CCGCGGGGAT | AAAATGTCAC | AAAATTCATT | TGGATCCTCA | CTCTCTTCAT | TTAAATATCC 2340 |
| CATACCCTTC | CTCCATCTAT | ACCACCCTAC | TCTCCTTTCC | TCATTATTCC | TCCTATTATC 2400 |
| TTCTCCTCTT | CTCTCCTTCT | TCTATATTTC | CCAAATCTAT | CATCATTCAC | TCTCATCCCC 2460 |
| TCTTCCTTCA | CTCCCATTCT | ATTCTACTCC | TTTCCCTTTC | CATATCCCCT | CCACCCCCCT 2520 |
| TCCTCCCCTC | TTTCAATCTT | ATCCCCAATC | ATAAAATTAT | CTCAATTATA | TTCTCCTTCC 2580 |
| ATACCCCCTA | TCATCCTCAT | CCCTATCACC | CCCTACTCAC | CCAATACTCC | CTACTCATCT 2640 |
| CATATATCCT | TATCCTCTCC | TCACCTCTCC | CTCCTCTATC | TCCCCCCCTC | ACACTCATTT 2700 |
| CTCATTCCAC | TCCCAAATAT | CCCATACCCT | TCCTCCATCT | ATACCACCCT | ACTCTCCTTT 2760 |
| CCTCATTATT | CCTCCTATTA | TCTTCTCCTC | TTCTCTCCTT | CTTCTATATT | TCCCAAATCT 2820 |
| ATCATCATTC | ACTCTCATCC | CCTCTTCCTT | CACTCCCATT | CTATTCTACT | CCTTTCCCTT 2880 |
| TCCATATCCC | CTCCACCCCC | CTTCCTCCCC | TCTTTCAATC | TTATCCCCAA | TCATAAAATT 2940 |
| ATCTCAATTA | TATTCTCCTT | CCATACCCCC | TATCATCCTC | ATCCCTATCA | CCCCCTACTC 3000 |
| ACCCAATACT | CCCTACTCAT | CTCATATATC | CTTATCCTCT | CCTCACCTCT | CCCTCCTCTA 3060 |
| TCTCCCCCCC | TCACACTCAT | TTCTCATTCC | ACTCCCGGGG | ATCAGCTTGG | CGTAATCATG 3120 |
| GTCATAGCTG | | | | | 3130 |

We claim:

1. A method of identifying a pharmacologically active substance, comprising
   a) providing a DNA template which comprises a target DNA sequence under the control of at least one gene-regulatory element,
   b) mixing with the template a nuclear extract and at least one labeled nucleotide,
   c) mixing with the template a candidate pharmacologically active substance,
   d) optionally removing the proteins from the reaction mixture after in vitro transcribing the DNA template,
   e) binding the labeled transcript to a solid matrix,
   f) removing the excess labeled nucleotides, and
   g) determining the amount of labeled transcript, relative to a control sample wherein said DNA template comprises unique cleavage sites for the restriction endonucleases PstI, EcoRI, SacI, KpnI, SacII, BamHI, SwaI, part of the plasmid pUC19, five binding sites for the yeast Gal4 protein, the "TATA" box of the human T-cell receptor Vβ8.1 between the SacII and BamHI restriction sites, the initiator region of the adenovirus major late promoter between the BAMHI and SwaI restriction sites, and a G-free sequence with a length of approximately 800 base pairs.

2. A method according to claim 1, wherein the DNA template is pGS100.

3. A method according to claim 1, wherein the DNA template has the sequence of SEQ ID NO. 1.

4. A method according to claim 1, wherein the universal reporter plasmid has been deposited under the DSM number 11450.

5. A DNA template, comprising unique cleavage sites for the restriction endonucleases PstI, EcoRI, SacI, KpnI, SacII, BamHI, SwaI, part of the plasmid pUC19, five binding sites for the yeast Gal4 protein, the "TATA" box of the human T-cell receptor Vβ8.1 between the SacII and BamHI restriction sites, the initiator region of the adenovirus major late promoter between the BAMHI and SwaI restriction sites, and a G-free sequence with a length of approximately 800 base pairs.

6. A DNA template according to claim 5 which is pGS100.

7. A DNA template according to claim 5 having the sequence of SEQ ID NO. 1.

8. A DNA template according to claim 5 which is deposited under the DSM number 11450.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
  (A) LENGTH: 3130 base pairs
  (B) TYPE: nucleic acid
  (C) STRANDEDNESS: double
  (D) TOPOLOGY: circular (ii) MOLECULE TYPE: DNA (genomic)

(ix) FEATURE:
    (A) NAME/KEY: exon
    (B) LOCATION: 1..3130

(xi) SEQUENCE DESCRIPTION: SEQ ID NO:1:

```
TTTCCTGTGT GAAATTGTTA TCCGCTCACA ATTCCACACA ACATACGAGC CGGAAGCATA      60

AAGTGTAAAG CCTGGGGTGC CTAATGAGTG AGCTAACTCA CATTAATTGC GTTGCGCTCA     120

CTGCCCGCTT TCCAGTCGGG AAACCTGTCG TGCCAGCTGC ATTAATGAAT CGGCCAACGC     180

GCGGGGAGAG GCGGTTTGCG TATTGGGCGC TCTTCCGCTT CCTCGCTCAC TGACTCGCTG     240

CGCTCGGTCG TTCGGCTGCG GCGAGCGGTA TCAGCTCACT CAAAGGCGGT AATACGGTTA     300

TCCACAGAAT CAGGGGATAA CGCAGGAAAG AACATGTGAG CAAAAGGCCA GCAAAAGGCC     360

AGGAACCGTA AAAAGGCCGC GTTGCTGGCG TTTTTCCATA GGCTCCGCCC CCCTGACGAG     420

CATCACAAAA ATCGACGCTC AAGTCAGAGG TGGCGAAACC CGACAGGACT ATAAAGATAC     480

CAGGCGTTTC CCCCTGGAAG CTCCCTCGTG CGCTCTCCTG TTCCGACCCT GCCGCTTACC     540

GGATACCTGT CCGCCTTTCT CCCTTCGGGA AGCGTGGCGC TTTCTCAATG CTCACGCTGT     600

AGGTATCTCA GTTCGGTGTA GGTCGTTCGC TCCAAGCTGG GCTGTGTGCA CGAACCCCCC     660

GTTCAGCCCG ACCGCTGCGC CTTATCCGGT AACTATCGTC TTGAGTCCAA CCCGGTAAGA     720

CACGACTTAT CGCCACTGGC AGCAGCCACT GGTAACAGGA TTAGCAGAGC GAGGTATGTA     780

GGCGGTGCTA CAGAGTTCTT GAAGTGGTGG CCTAACTACG GCTACACTAG AAGGACAGTA     840

TTTGGTATCT GCGCTCTGCT GAAGCCAGTT ACCTTCGGAA AAAGAGTTGG TAGCTCTTGA     900

TCCGGCAAAC AAACCACCGC TGGTAGCGGT GGTTTTTTTG TTTGCAAGCA GCAGATTACG     960

CGCAGAAAAA AAGGATCTCA AGAAGATCCT TTGATCTTTT CTACGGGGTC TGACGCTCAG    1020

TGGAACGAAA ACTCACGTTA AGGGATTTTG GTCATGAGAT TATCAAAAAG GATCTTCACC    1080

TAGATCCTTT TAAATTAAAA ATGAAGTTTT AAATCAATCT AAAGTATATA TGAGTAAACT    1140

TGGTCTGACA GTTACCAATG CTTAATCAGT GAGGCACCTA TCTCAGCGAT CTGTCTATTT    1200

CGTTCATCCA TAGTTGCCTG ACTCCCCGTC GTGTAGATAA CTACGATACG GGAGGGCTTA    1260

CCATCTGGCC CCAGTGCTGC AATGATACCG CGAGACCCAC GCTCACCGGC TCCAGATTTA    1320

TCAGCAATAA ACCAGCCAGC CGGAAGGGCC GAGCGCAGAA GTGGTCCTGC AACTTTATCC    1380

GCCTCCATCC AGTCTATTAA TTGTTGCCGG GAAGCTAGAG TAAGTAGTTC GCCAGTTAAT    1440

AGTTTGCGCA ACGTTGTTGC CATTGCTACA GGCATCGTGG TGTCACGCTC GTCGTTTGGT    1500

ATGGCTTCAT TCAGCTCCGG TTCCCAACGA TCAAGGCGAG TTACATGATC CCCCATGTTG    1560

TGCAAAAAAG CGGTTAGCTC CTTCGGTCCT CCGATCGTTG TCAGAAGTAA GTTGGCCGCA    1620

GTGTTATCAC TCATGGTTAT GGCAGCACTG CATAATTCTC TTACTGTCAT GCCATCCGTA    1680

AGATGCTTTT CTGTGACTGG TGAGTACTCA ACCAAGTCAT TCTGAGAATA GTGTATGCGG    1740

CGACCGAGTT GCTCTTGCCC GGCGTCAATA CGGGATAATA CCGCGCCACA TAGCAGAACT    1800

TTAAAAGTGC TCATCATTGG AAAACGTTCT TCGGGGCGAA AACTCTCAAG GATCTTACCG    1860

CTGTTGAGAT CCAGTTCGAT GTAACCCACT CGTGCACCCA ACTGATCTTC AGCATCTTTT    1920

ACTTTCACCA GCGTTTCTGG GTGAGCAAAA ACAGGAAGGC AAAATGCCGC AAAAAAGGGA    1980

ATAAGGGCGA CACGGAAATG TTGAATACTC ATACTCTTCC TTTTTCAATA TTATTGAAGC    2040

ATTTATCAGG GTTATTGTCT CATGAGCGGA TACATATTTG AATGTATTTA GAAAAATAAA    2100

CAAATAGGGG TTCCGCGCAC ATTTCCCCGA AAAGTGCCAC CTGGGGGACT AGAGTCTCCG    2160

CTCGGAGGAC AGTACTCCGC TCGGAGGACA GTACTCCGCT CGGAGGACAG TACTCCGCTC    2220
```

-continued

```
GGAGGACAGT ACTCCGCTCG GAGGACAGTA CTCCGACCTG CAGGAATTCG AGCTCGGTAC      2280

CCGCGGGGAT AAAATGTCAC AAAATTCATT TGGATCCTCA CTCTCTTCAT TTAAATATCC      2340

CATACCCTTC CTCCATCTAT ACCACCCTAC TCTCCTTTCC TCATTATTCC TCCTATTATC      2400

TTCTCCTCTT CTCTCCTTCT TCTATATTTC CCAAATCTAT CATCATTCAC TCTCATCCCC      2460

TCTTCCTTCA CTCCCATTCT ATTCTACTCC TTTCCCTTTC CATATCCCCT CCACCCCCCT      2520

TCCTCCCCTC TTTCAATCTT ATCCCCAATC ATAAAATTAT CTCAATTATA TTCTCCTTCC      2580

ATACCCCCTA TCATCCTCAT CCCTATCACC CCCTACTCAC CCAATACTCC CTACTCATCT      2640

CATATATCCT TATCCTCTCC TCACCTCTCC CTCCTCTATC TCCCCCCCTC ACACTCATTT      2700

CTCATTCCAC TCCCAAATAT CCCATACCCT TCCTCCATCT ATACCACCCT ACTCTCCTTT      2760

CCTCATTATT CCTCCTATTA TCTTCTCCTC TTCTCTCCTT CTTCTATATT TCCCAAATCT      2820

ATCATCATTC ACTCTCATCC CCTCTTCCTT CACTCCCATT CTATTCTACT CCTTTCCCTT      2880

TCCATATCCC CTCCACCCCC CTTCCTCCCC TCTTTCAATC TTATCCCCAA TCATAAAATT      2940

ATCTCAATTA TATTCTCCTT CCATACCCCC TATCATCCTC ATCCCTATCA CCCCCTACTC      3000

ACCCAATACT CCCTACTCAT CTCATATATC CTTATCCTCT CCTCACCTCT CCCTCCTCTA      3060

TCTCCCCCCC TCACACTCAT TTCTCATTCC ACTCCCGGGG ATCAGCTTGG CGTAATCATG      3120

GTCATAGCTG                                                             3130
```